(12) United States Patent
Lasorso, Jr.

(10) Patent No.: US 9,457,166 B1
(45) Date of Patent: Oct. 4, 2016

(54) PHYSICAL THERAPY WHOLE SOUND FREQUENCIES DEVICE AND METHOD OF RECORDING CONTENT USED THEREIN

(71) Applicant: Vincent J. Lasorso, Jr., Cincinnati, OH (US)

(72) Inventor: Vincent J. Lasorso, Jr., Cincinnati, OH (US)

( * ) Notice: Subject to any disclaimer, the term of this patent is extended or adjusted under 35 U.S.C. 154(b) by 66 days.

(21) Appl. No.: 14/456,215

(22) Filed: Aug. 11, 2014

Related U.S. Application Data

(63) Continuation-in-part of application No. 12/324,990, filed on Nov. 28, 2008, now Pat. No. 8,801,591.

(60) Provisional application No. 60/990,802, filed on Nov. 28, 2007.

(51) Int. Cl.
*A61H 23/00* (2006.01)
*A61M 21/02* (2006.01)

(52) U.S. Cl.
CPC .............. *A61M 21/02* (2013.01); *A61H 23/00* (2013.01)

(58) Field of Classification Search
CPC ................ A61H 23/0236; A61H 2201/0149; A61H 2201/0138; A61H 2201/5048; A61H 23/0245; H04R 5/023; H04R 2400/03; A61B 17/22004; A61B 17/22012; A61M 2021/0022; A61M 2021/0027
See application file for complete search history.

(56) References Cited

U.S. PATENT DOCUMENTS

| | | | |
|---|---|---|---|
| 3,556,088 A | 1/1971 | Leonardini | |
| 3,880,152 A | 4/1975 | Nohmura | |
| 4,064,376 A | 12/1977 | Yamada | |
| 4,216,766 A | 8/1980 | Duykers et al. | |
| 6,027,463 A | 2/2000 | Moriyasu | |
| 6,702,767 B1 * | 3/2004 | Douglas | A61M 21/0094 600/21 |
| 7,232,417 B2 | 6/2007 | Plante | |
| 7,402,922 B2 | 7/2008 | Springer et al. | |
| 2004/0097851 A1 * | 5/2004 | Inada | A61H 23/0254 601/47 |
| 2005/0226449 A1 * | 10/2005 | Young | A61H 23/0236 381/333 |

OTHER PUBLICATIONS

First office action on the merits (Non-Final Rejection) in U.S. Appl. No. 12/324,990, sent on Dec. 12, 2011.
Second office action on the merits (Final Rejection) in U.S. Appl. No. 12/324,990, sent on May 9, 2012.
Third office action on the merits (Non-Final Rejection) in U.S. Appl. No. 12/324,990, mailed on Sep. 23, 2013.
The Acoustopathic Healing System, White Willow Tai Chi Website, Web page <http://www.whitewillowtaichi.com/home/acoustopathic_healing.html>, 2 pages, dated Nov. 27, 2011, retrieved from Internet Archive Wayback Machine <https://web.archive.org/web/20111127032820/http://www.whitewillowtaichi.com/home/acoustopathic_healing.html> on Aug. 29, 2014.
Wholisound Serenity Box, My Serenity Box Website, Web page <http://www.myserenitybox.com>, 1 page, dated Oct. 30, 2012, retrieved from Internet Archive Wayback Machine <https://web.archive.org/web/20121030134207/http://www.myserenitybox.com> on Oct. 3, 2014.

* cited by examiner

*Primary Examiner* — Christine H Matthews
*Assistant Examiner* — Joshua D Lannu
(74) *Attorney, Agent, or Firm* — The Law Office of Patrick F. O'Reilly III, LLC

(57) ABSTRACT

The present invention includes a device and method for relaxing and promoting healing to an individual by synchronization of kinesthetic and aural whole tone sounds.

17 Claims, 7 Drawing Sheets

PHYSICAL THERAPY WHOLE SOUND FREQUENCIES DEVICE AND METHOD OF RECORDING CONTENT USED THEREIN

CROSS-REFERENCE TO RELATED APPLICATIONS

This is a continuation-in-part of U.S. Nonprovisional patent application Ser. No. 12/324,990, entitled "Physical Therapy Whole Sound Frequencies Device and Method of Using the Same", filed Nov. 28, 2008, and further claims the benefit of U.S. Provisional Patent Application No. 60/990,802, entitled "Physical Therapy Whole Sound Frequencies Device and Method of Using the Same", filed Nov. 28, 2007, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to improved individual health and well-being based upon vibrational energies, and more particularly relates to physical and auditory stimulation of biological tissue through whole sound frequencies and harmonics.

2. Background and Description of Related Art

When a cell of any living organism is confronted with a source of stress, the cell constricts itself to avoid impact. Such response has been referred to as "bracing."

Substantially, all cells within the human body react the same when they are confronted with a stressor. Whether that stressor is mechanical activity, chemical, electrical, viral, or bacterial, the cell typically reduces its respective size to limit exposure to injury. When the stressor is removed, the cell returns to its normal pre-stress size. If the stressor is not removed, the cell will typically maintain its reduced size until the cell exhausts its internal resources and fails.

The average human body is confronted with numerous stressors, including, for example, sound, vibrations, temperature, pollution, and electromagnetic radiation. Skin and the musculoskeletal system typically absorb such stressors to defend inner workings of the body. However, the same inner workings are also assaulted by ingested and absorbed toxins, which also result in bracing through many systems of the body.

A human mind is also a generator of stressors. The mind interprets interpersonal and social activities and interactions as "threats" to its emotional well-being. Such cognitive threats create hormonal "fight or flight" reactions causing cellular bracing substantially throughout the body.

Cells of the body are connected by a web of connective tissue called the extracellular matrix (ECM). The ECM provides a space between cells called the interstitial space, where the exchange of nutrients and waste occurs. The ECM is patrolled by large leukocytes exterminating invading viruses, bacteria, and damaged or cancerous cells. As cells brace, they become more rigid and impenetrable to invaders as well as chemicals and nutrients necessary for cell health. Bracing cells pull upon the connective tissues of the ECM, thereby narrowing space between cells. Such diminished space, first prevents the leukocytes from patrolling the space, then diminishes the exchange of waste and nutrients and finally, when the space becomes too narrow, creates an inflammatory process resulting in death of existing cells and malformation of regenerated cells.

The most common experience of bracing is myofascial tension and pain causing secondary arthritis and joint destruction. The average body responds to the external stressors of its environment and the inner stressors of the mind, by tensing muscle fibers. If cells are consistently exposed to similar stressors, the cells will adapt by maintaining the braced state, even when the stressor is absent. Such chronic adaptation is called "habitual bracing." Habitual bracing defines the new baseline of muscle length within the stretch receptors of the muscle spindles and the proprioception model of the brain. The body "believes" that any less tension leaves it vulnerable. Since the base line within the brain and stretch receptors has been modified, the body no longer notices the "tension" among the cells, thereby shortening and misaligning associated muscles. The habitual bracing of any muscle group within the muscle skeletal system begins a slow degenerative process of the entire organism.

A muscle group that shortens, due to a stressor, may put adjacent muscles and joints into a state of tension, and becomes a secondary stressor to those fibers. Over time, the adjacent muscles and joints may begin to adapt into habitual bracing.

Both movement and stabilization of the body is generated by a harmonizing polarity between agonist and antagonistic muscle groups; one in action, and the other in repose. The habitual bracing and shortening of a group of muscles may also stress its complimentary antagonist. Eventually the baseline and proprioceptive model of the entire body is changed, and may adversely affect joint alignment, range of motion, and balance. It should be noted that as new stressors are added, the muscles respond once again by bracing from their now shortened baseline. And as before, consistent exposure can create a new habitual baseline. At some point, the muscles braces to a length which stimulates neural pain receptors in the muscle. When a nerve is continually over stimulated, the nerve will habitually create a chronic pain response.

Aside from movement of the associated body, muscles are the primary means of propelling blood through veins and fluids through the aforementioned interstitial spaces. Blood moves from the capillary beds and into the veins by pressurized displacement from newly arrived arterial blood. Once in the veins, muscular action and one-way valves move the blood until it reaches larger muscular veins. Inadequate muscular action can begin the process of peripheral artery disease and blood clots.

The motility of the interstitial fluid is the means in which waste is transported into the lymphatic system and ultimately out of the body. Substantially all cellular metabolism and immune response is dependent upon the interstitial flow. Muscles in habitual bracing are often no longer able to adequately expand and contract in a full enough range to efficiently squeeze the interstitial fluids entirely out of the lymph capillaries leaving the body very vulnerable to disease.

As the external muscles change shape and position they also change the internal space and pressures affecting the function of vital organs including the brain.

Bracing along the spine, back, and chest may inhibit respiration, intestinal motility, organ flow, and output. However, bracing has it most profound effects upon the brain.

Bracing of the head and spinal column influences brain functioning in three important ways.

First, the muscles around the skull can inhibit the exchange of cerebral spinal fluid (CSF) into the veins of the sub-arachnoid granulations, i.e., the blood/brain gateway/barrier, by increasing venous pressure. Thus, the dissemination of hormones into the blood stream of the body is diminished.

Second, the muscles around the base of the skull and the neck can displace and torque the cervical vertebra applying tension in the meninges, thereby increasing intra-cranial pressure upon the brain, diminishing cognitive functioning, and inhibiting CSF exchange across the blood/brain barrier, and circulation of CSF through the brain's ventricles.

Third, bracing of the spine from lumbar to the skull reduces the flexion pumping action of CSF from the lumbar reservoir into the ventricles of the inner brain called the cerebral-spinal pump (CSP). The CSF circulates within the spaces of the brain disseminating nutrients, hormones, neurotransmitters and eliminating waste. The CSF cleans, nourishes and protects the brain and spinal cord. Clean circulating fluid is essential to insure proper transmission of neurotransmitters across the neuro-synaptic gaps. Waste products prevent transfer and reuptake of neurotransmitters, resulting in cognitive and emotional dysfunction. The cleanliness of the CSF is so important that the body produces three times its volume each day, with old fluid draining into the lymphatic system.

The circulation of CSF by the CSP performs two other functions. In particular, the circulation stimulates the lower brain stem and cerebellum and disseminates non-differeniated stem cells. Non-differentiated stem cells repair damaged regions of the brain and differentiate to create new brain where neural demand is large.

Stressors change the physical environment of the cells. The bracing reaction is in turn a physical reaction to an unhealthy environment. There is no chemical or intercellular mechanism to relax a braced cell. The cells will only relax via mechanical action upon the integrins. The integrins attach to the ECM and pass through the cellular membrane into the nucleus and the DNA itself. Physical, pulsating messages of an expanding relaxing ECM convince the nucleus to let go of its protective tension. For this reason the best way to release physical stress is through movement, stretching and physical manipulations, e.g. massage, rolfing, and the like.

With a simple glance at an anatomy chart one quickly observes that muscle groups and fibers freely pass under, over, and even through each other. Given that stressors do not uniformly affect all muscle fibers equally within a muscle, and that all muscle fibers within a muscle do not receive an equal amount of movement, a pathological condition occurs which we call "binding." Binding occurs when braced; shortened fibers of a muscle impede another fiber from moving along its normal vector or through its complete contraction/relaxation range. The binding itself becomes a source of stress and low grade inflammation, progressing to a state of actually stopping the movement of some fibers of the muscle. Pathology, historically known as "muscle bound," occurs when a region of the muscle becomes effectively immobile and sometimes literally bounded by other fibers within it. These regions are also known as "knots" and "trigger points." Bounded sections of muscles are "splinted" from the actions of movement, exercise, and stretching which would normally release the bracing. The bound sections rarely respond completely to classical "rubbing" or mechanical vibrating massage because the reset stretch receptors only release to the shortened length. The fibers have to be manually released and repositioned by deep tissue therapies, which may include the use of Botox or surgery.

One means for releasing such binding and bracing is through the use of sound. Physical and psychological therapy using sounds is not a new concept. Pythagoras, the Greek mathematician and philosopher, codified tones, intervals, and modes of sound that tended to best heal, unify, and create a balanced mind and body. This work by Pythagoras has become a foundation of western music, science, holistic homeopathic medicine, and religion.

Disciples of Pythagoras mastered a mind and body connection through chanting and lyre playing. In doing so, diseases healed, bodies were conditioned, and minds and bodies were elevated. The ongoing work of Pythagoras' work unlocked secret mathematical proportions and energies of the universe, and therein resulted formulae for health, longevity, physical transformation, and spiritual ascension.

In the current era, vibrational noise has been used to heal individuals, both of mind and body. However, typical such vibrational noise therapy is of a single vibrating frequency.

Vibroacoustic therapy is a known method of playing music or other tones through an object to vibrate an individual's body to relieve pain and/or anxiety, and to induce healing.

What is needed is a device and method for relaxing and promoting healing of an individual through a mixture of vibrational energy and sound.

BRIEF SUMMARY OF EMBODIMENTS OF THE INVENTION

Accordingly, the present invention is directed to a physical therapy whole sound frequencies device and a method of using the same that substantially obviates one or more problems resulting from the limitations and deficiencies of the related art.

In accordance with one or more embodiments of the present invention, there is provided a device for relaxing and promoting healing of biological tissue. The device is comprised of an inputting means configured to generate a digital signal based upon one or more predetermined acoustic whole sounds introduced to the inputting means, and one or more vibrational units connected to the inputting means. The predetermined acoustic whole sounds include harmonic sound content with a root frequency, a plurality of overtone frequencies that are greater than the root frequency and mathematically proportional to the root frequency, and a plurality of undertone frequencies that are less than the root frequency and mathematically proportional to the root frequency. At least one of the plurality of overtone frequencies and the plurality of undertone frequencies of the harmonic sound content is substantially identical to the proportional harmonic frequencies of body cells and/or molecules such that the one or more predetermined acoustic whole sounds are configured to engage and direct the body cells and/or molecules of human beings through the harmonic sound content. The one or more vibrational units have a processing device configured to generate frequency pulse waves based upon the digital signal relayed by the connected inputting means, and one or more transducers configured to vibrate the one or more vibrational units using the one or more predetermined acoustic whole sounds effective to transfer the one or more predetermined acoustic whole sounds into one or more of bones, tissues or peripheral nerves of an individual. The device further includes at least one auditory relay unit connected to the inputting means. The at least one auditory relay unit having speakers for transferring an auditory signal associated with the digital signal of the inputting means. The one or more vibrational units and the at least one auditory relay unit are configured to be placed in contact with the individual for a predetermined period of time.

In a further embodiment of the present invention, the inputting means comprises one of: (i) a personal digital music player, (ii) a compact disc (CD) player, (iii) a digital video disc (DVD) player, (iv) a smartphone, (v) a digital tablet device, and (vi) a personal computing device.

In yet a further embodiment, the inputting means is external to the one or more vibrational units, and wherein the inputting means is operatively coupled to the one or more vibrational units by means of one or more electrical cords or a wireless connection.

In still a further embodiment, the inputting means is disposed inside a housing of the one or more vibrational units.

In yet a further embodiment, the one or more vibrational units comprise a housing, the housing of each of the one or more vibrational units being in the shape of either a generally rectangular box or a generally wedge-shaped box configured to be disposed underneath a portion of a body of the individual.

In still a further embodiment, the auditory relay unit comprises one of: (i) a pair of audio headphones, (ii) a pair of audio speakers, and (iii) a combination of audio headphones and audio speakers.

In accordance with one or more other embodiments of the present invention, there is provided a method for relaxing and promoting healing of biological tissue. The method is comprised of the steps of: (i) positioning a device adjacent to an individual's body; (ii) positioning at least one auditory relay unit proximate to, or on a first portion of the individual's body; (iii) positioning one or more vibrational units proximate to, or in contact with a second portion of the individual's body; and (iv) transmitting one or more predetermined acoustic whole sounds to the first and second portions of the individual's body for a predetermined period of time using the at least one auditory relay unit and the one or more vibrational units. The device is comprised of an inputting means configured to generate a digital signal based upon one or more predetermined acoustic whole sounds introduced to the inputting means, and one or more vibrational units connected to the inputting means. The predetermined acoustic whole sounds include harmonic sound content with a root frequency, a plurality of overtone frequencies that are greater than the root frequency and mathematically proportional to the root frequency, and a plurality of undertone frequencies that are less than the root frequency and mathematically proportional to the root frequency. At least one of the plurality of overtone frequencies and the plurality of undertone frequencies of the harmonic sound content is substantially identical to the proportional harmonic frequencies of body cells and/or molecules such that the one or more predetermined acoustic whole sounds are configured to engage and direct the body cells and/or molecules of human beings through the harmonic sound content. The one or more vibrational units have a processing device configured to generate frequency pulse waves based upon the digital signal relayed by the connected inputting means; and one or more transducers configured to vibrate the one or more vibrational units using the one or more predetermined acoustic whole sounds effective to transfer the one or more predetermined acoustic whole sounds into one or more of bones, tissues or peripheral nerves of the individual. The device further includes at least one auditory relay unit connected to the inputting means. The at least one auditory relay unit having speakers for transferring an auditory signal associated with the digital signal of the inputting means.

In a further embodiment of the present invention, the step of positioning the at least one auditory relay unit comprises positioning the at least one auditory relay unit on the head of the individual's body.

In yet a further embodiment, the step of positioning the one or more vibrational units comprises positioning the one or more vibrational units adjacent to one or more limbs of the individual's body.

In still a further embodiment, the step of positioning the at least one auditory relay unit comprises positioning the at least one auditory relay unit at a first end of the individual's body, and wherein the step of positioning the one or more vibrational units comprises positioning the one or more vibrational units at a second end of the individual's body, the first end of the individual's body being disposed generally opposite to the second end of the individual's body.

In accordance with yet one or more other embodiments of the present invention, there is provided a method for relaxing and promoting healing of biological tissue. The method is comprised of the steps of: (i) positioning a device adjacent to an individual's body; (ii) positioning at least one auditory relay unit proximate to, or on a first portion of the individual's body; (iii) positioning one or more vibrational units proximate to, or in contact with a second portion of the individual's body; and (iv) transmitting one or more predetermined acoustic whole sounds to the first and second portions of the individual's body for a predetermined period of time using the at least one auditory relay unit and the one or more vibrational units. The device is comprised of an inputting means configured to generate a digital signal based upon one or more predetermined acoustic whole sounds introduced to the inputting means, and one or more vibrational units connected to the inputting means. The predetermined acoustic whole sounds include proportional harmonic overtone frequencies and a plurality of message templates, each of the plurality of message templates comprising harmonic sound content configured to have a predetermined targeted effect on tissues and cells of human beings. The one or more vibrational units have a processing device configured to generate frequency pulse waves based upon the digital signal relayed by the connected inputting means; and one or more transducers configured to vibrate the one or more vibrational units using the one or more predetermined acoustic whole sounds effective to transfer the one or more predetermined acoustic whole sounds into one or more of bones, tissues or peripheral nerves of the individual. The device further includes at least one auditory relay unit connected to the inputting means. The at least one auditory relay unit having speakers for transferring an auditory signal associated with the digital signal of the inputting means.

In a further embodiment of the present invention, the plurality of message templates of the one or more predetermined acoustic whole sounds comprises one or more infrasonic message templates. In addition, the step of transmitting the one or more predetermined acoustic whole sounds further comprises directly transmitting the one or more infrasonic message templates to the individual's body using the one or more vibrational units, and indirectly transmitting the one or more infrasonic message templates to the individual's body using the at least one auditory relay unit.

In yet a further embodiment, the one or more predetermined acoustic whole sounds further comprise harmonic sound content with a root frequency, a plurality of overtone frequencies that are greater than the root frequency and mathematically proportional to the root frequency, and a plurality of undertone frequencies that are less than the root frequency and mathematically proportional to the root frequency. At least one of the plurality of overtone frequencies and the plurality of undertone frequencies of the harmonic sound content is substantially identical to the proportional harmonic frequencies of body cells and/or molecules. In addition, the step of transmitting the one or more predetermined acoustic whole sounds further comprises transmitting the one or more predetermined acoustic whole sounds to the individual's body so as to engage and direct the body cells and/or molecules of the individual through the harmonic sound content.

In still a further embodiment, the step of positioning the at least one auditory relay unit comprises positioning the at least one auditory relay unit on the head of the individual's body.

In yet a further embodiment, the step of positioning the one or more vibrational units comprises positioning the one or more vibrational units adjacent to one or more limbs of the individual's body.

In still a further embodiment, the step of positioning the at least one auditory relay unit comprises positioning the at least one auditory relay unit at a first end of the individual's body, and wherein the step of positioning the one or more vibrational units comprises positioning the one or more vibrational units at a second end of the individual's body, the first end of the individual's body being disposed generally opposite to the second end of the individual's body.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
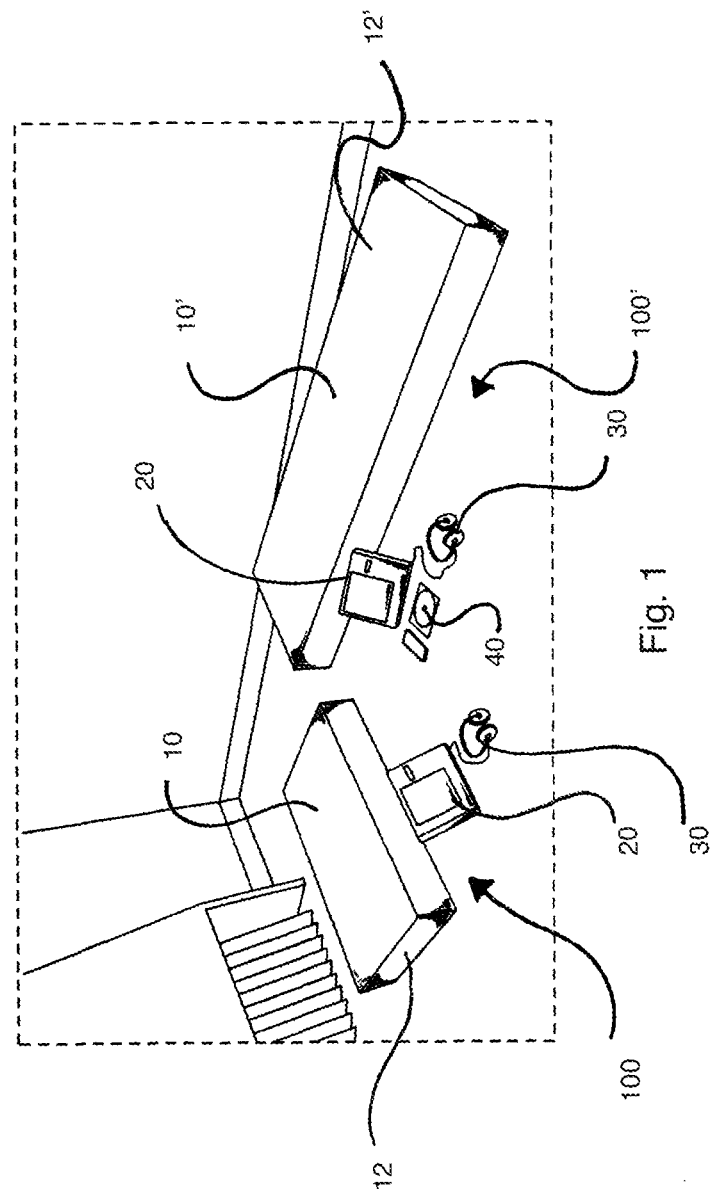
FIG. 1 is a perspective view illustrating first and second exemplary embodiments of the physical therapy whole sound frequencies device.

The various exemplary embodiments of the present invention include a device, system, and method for relaxing and promoting healing of biological tissue of an individual. The various exemplary embodiments include an inputting means for introduction of predetermined acoustic sound.

A true "sound" as used herein is comprised of proportional frequencies working in harmony to create a single perceivable tone. Such proportional frequencies are substantially identical to the proportional frequencies of bodies, cells, and molecules of individuals.

Typical vibrational noise replicators, that is, for example, massagers, vibrators, and the like, produce perceived positive results on the body by actually attacking the body. These vibrational noise replicators are usually mechanical in nature and induce regular pulsing waves into the individual's body which violently stresses cells of the individual. Such violent stressing of the cells forces the cells into a bracing protective mode.

In the first several minutes of such stressing upon the cells, a body's adaptive responses produce deep level tension that can lead to positive strengthening. However, after a short period of time, typically about ten minutes, the adaptive responses start to fail in resisting the regular pulsing waves and the adaptive responses "let go" of body tension out of sheer exhaustion. After about twenty more minutes of such regular pulsing waves, a cellular destructive cycle initiates.

Various exemplary embodiments of the present invention include a sound delivery system. The preferred system transfers substantially full harmonic, acoustically generated, structured sound (whole sounds) vibration into an individual's body to orchestrate systemic functions of the tissues, fluids, and nervous system in order to release and reverse the negative effects of bracing. Whole sounds are specifically engineered by frequency and modulation to preferably achieve a targeted predictable effect upon tissues and structures.

It is preferred that the whole sounds are simultaneously delivered to the body though various senses: aurally into the central nervous system of the brain; conductively through the bones; acoustically through the bodily fluids and spaces; and piezoelectrically through bands of connective tissue and peripheral mechanoreceptors (sensory nerves). The simultaneous stimulation of a combination or substantially all of these bodily systems with the whole sounds, accesses and releases bracing in many or all manner of tissue. Such accessing and releasing resets the original proprioceptive values on muscle length and position re-ordering the body to its "normal" functioning and range of motion.

The various exemplary embodiments may use uses a Primary Sound Delivery Unit (PSDU) or vibrational unit, which, through substantially direct contact with a body, preferably transfers whole sound vibrations into bones, tissues, and peripheral nerves of the body. The PSDU has four preferred configurations: a platform upon which an individual may sit, lay, and/or exercise upon; a notebook-sized box plate; a contoured wedge-shape device to be placed under an individual's feet, under an individual's legs, or upon an individual's back; and a neck device to be worn over an individual's shoulders and in contact with the back of the individual's neck.

The PSDU includes transducers to vibrate the unit using whole sounds. The PSDU is attached to a substantially solid surface that preferably will directly contact the individual's body. The sound moves into the tissues activating the mechanoreceptors of the nervous system and integrins of the cells. The vibration then moves into the bones and is conducted throughout the entire skeletal system. It is through the bones that all the tissues of the body are accessed.

Striated muscle connects to bones via tendons. The sound of the present exemplary embodiments is transferred through the tendons directly to spindles of the striated muscles of the individual's body. Such transfer allows the signal to bypass any resistance from bracing or muscle binding that would prevent release from occurring through massage or exercise.

A shortened muscle will naturally be in tension across its body to the points at which the muscle attaches to the skeletal frame. This normally pathological state becomes therapeutic with the introduction of whole sound. The tension provides a traction vector elongating the muscle to its normal length while the sound, through an orchestrated combination of frequency and modulation, acts upon the mechanoreceptors of the muscle spindle, to release the tension of the muscle. The muscle spindle, with its reset pathological bracing proprioceptive length value, under normal circumstances would react with pain at an attempt to restore it to its non-pathological condition.

Pain is gated from being experienced through the simultaneous actions of: over-stimulation of sensory pain mechanoreceptors in the skin and connective tissue; over-stimulation of pain receptors within the skeletal structure; aural stimulation of the brain with binaural beats creating a frequency following response that alters cognitive perception in a manner to not perceive pain; rhythmic patterned stimulation of the cerebellum by the simultaneous application of whole sound through the auditory cortex and physical vibration of the organ via acoustic fluid pulsations of the CSF in a manner to trigger the release of endorphins and dopamine.

The majority of bracing occurs while the human body is in a vertical orientation, that is, wherein a longitudinal axis of the human body is substantially perpendicular to the ground while standing or sitting. The vector on which the shortening occurs is the axis with the maximum amount traction on the spindles requiring release. Sound conductivity through the bone is at its maximum effectiveness, for responsiveness and transmission, along the longitudinal axis of the bone perpendicular to the PSDU.

For these stated reasons, re-establishing the pre-pathology length of striated muscle is greatly enhanced by the performance of stretching, range-of-motion exercises, Yoga, Pilates or Qigong while sitting or standing upon the platform versions of the invention. Movements in combination with traction increase the stimulation on the mechanoreceptors and speeds the process of muscle release. Torsional and rotational movement of an individual's limbs, clockwise and counter-counter clockwise around the longitudinal axis, unwinds the muscles in their natural lines of contraction, and are therefore, more effective than movements parallel to the bone axis.

An increase in strength is created almost immediately with the first application of whole sound, under all frequencies and modulations, and continues to increase through a three phase learning process: the frequencies release the muscle bracing to normal lengths allowing the muscle full use of all its fibers along its entire length; the vibration of the sound decreases resistance within and between fascias of adjacent muscles; and the consistent vibration causes all local cells to harmonize and entrain to each other through the localized communication system of the integrin and connective tissue network, training and recruiting local fibers and muscle groups to work as a cohesive, coherent, connective unit making more fibers available for any given task. The new localized community reorganizes the neural pathways of the sensory motor cortex to create new permanent patterns. Strength may also be created by utilizing frequencies and modulations below about 50 Hertz that cause low intensity, short duration stress to cells causing a natural, strengthening, bracing contraction immediately followed by a relaxation phase for recovery. This passive cellular exercise can be especially effective on those who are physically infirmed.

Bone density and strength is created through the same passive cellular exercise. Bone strength and density is also increased naturally in reaction to the increased stressors applied to the bone structures by the now stronger musculature. As muscle fibers are relaxed, resistance between articulating bone surfaces are reduced and the muscle stress is redirected to their natural tendon attachments along the bone's surface. The natural, more evenly distributed muscle stress activates more osteoblasts along the length of the bone, creating an even growth and density of new bone. With the relief of pressure on articulating bone surfaces, the cartilage, with or without, nutritional supplementation, has the opportunity to regenerate.

Various exemplary embodiments of the present invention include the potential for neural regeneration. Fine, discrete, nuanced motor control, i.e., skill, over the muscles of the body to perform detailed tasks of sport, art, music, etc. is achieved from thousands of repetitions of the movement patterns which in turn increase neural density within the regions of the sensory motor cortex of the brain that is responsible for generating the movements. Numerous repetitions of a task overload the sensory and motor neurons forcing each to recruit other neurons of the brain to take the load. This is analogous to a business hiring temporary workers during a busy season. As training continues over the course of days, the neurons of the motor cortex, like striated muscle cells, send out a signal for new brain cells to be permanently assigned. Unlike muscle cells, brain cells are born from non-differentiated stem cells floating in reserve in the CSF filled ventricles of the mid-brain. The stem cells swim through the CSF to the region of the motor cortex requesting cells. The stem cells differentiate to become permanently dedicated motor cells. Current research suggests that the brain repairs and expands itself only in reaction to increased, sustained, concentrated, demand for many hours per day over the course of many days.

The invention, in all its configurations, stimulates brain repair and expansion of neurons by: simultaneously overloading the entire sensory motor cortex, neo cortex, auditory cortex, and cerebellum, limiting the amount of available neurons for recruitment to execute a training or rehabilitation pattern, accelerating the request for stem cells; inducing a physiological "relaxation response" creating a fertile, environment for cellular differentiation; guiding the brain to a theta dominant brain wave state, diminishing chaotic cognitive chatter to enhance neural focus upon the training pattern; and stimulating the circulation of CSF insuring a clean, unobstructed medium for efficient stem cell travel from ventricle to location of demand.

The device of the exemplary embodiments herein synergistically stimulates an individual through kinesthetic sound by way of a vibrational unit and through aural sound by way of an auditory relay unit.

Figure 4:
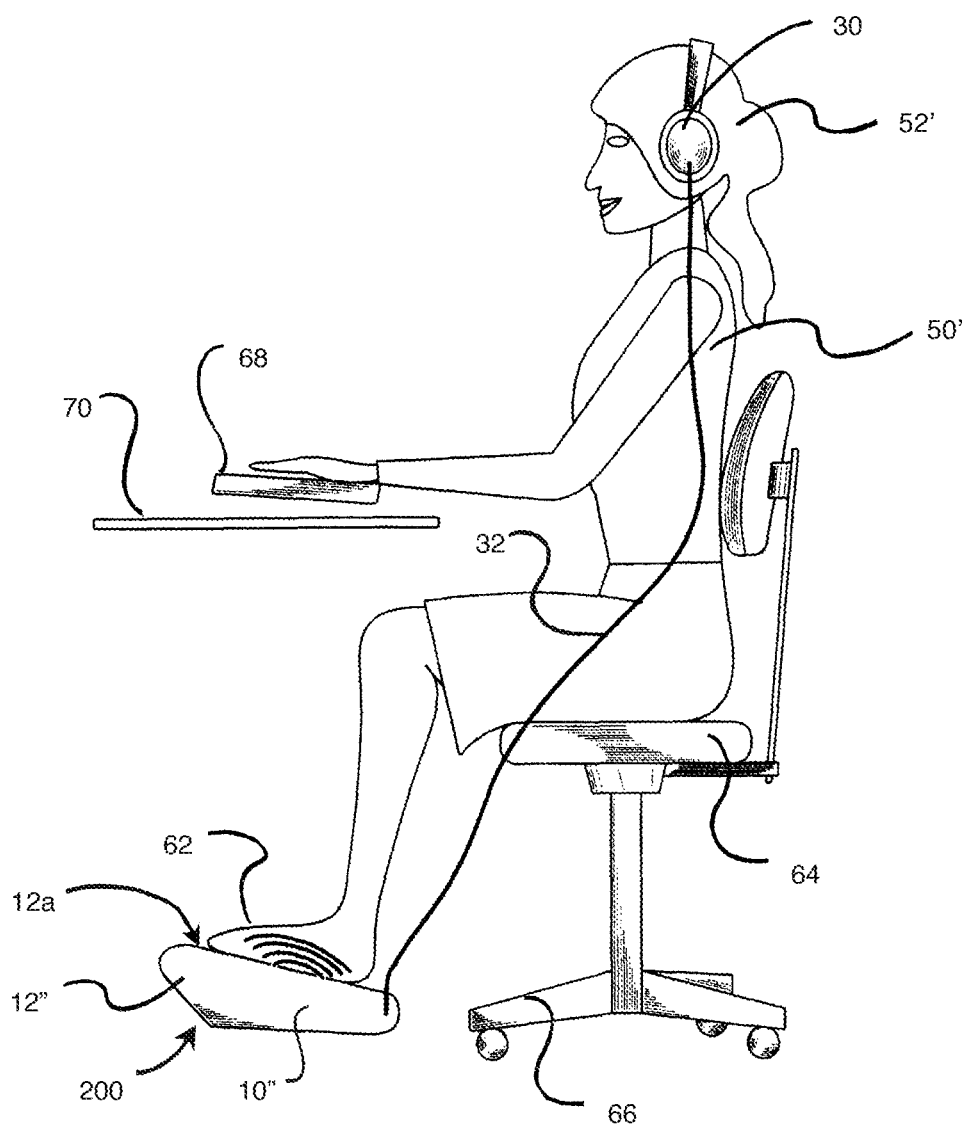
FIG. 4 is a side view illustrating an individual utilizing the third exemplary embodiment of the physical therapy whole sound frequencies device.

The auditory relay unit, as illustrated in FIG. 4, may be in the form of a personal digital music player. Other examples of inputting means may include compact disc (CD) players, digital video disc (DVD) players, mp3 format players, mp4 format players, personal computer system, or other similar unknown sound transmitter.

The auditory relay unit in the various exemplary embodiments preferably provides acoustical sounds which include sounds produced by one or more acoustical musical instruments, one or more human voices, one or more animal voices, or a combination thereof. Acoustical sounds are preferred because the sounds typically are not considered "droning" and include natural overtones.

In the various exemplary embodiments, the auditory relay unit is connected to one or more vibrational units. Exemplary vibrational units are illustrated in FIGS. 1-6.

Each vibrational unit preferably includes a user interface to manipulate the functioning of the respective vibrational unit. An exemplary user interface may include a power control, an amplitude control, and the like.

Each vibrational unit of the exemplary embodiments of the present invention also includes a processing means. The processing means generates frequency pulse waves based upon the digital signal relayed by the connected inputting means. Such processing means may be in the form of, for example, a microprocessor.

The processing means of the one or more vibrational units is connected to a vibrating means to produce vibrational energy that may be transferred to adjacent and/or substantially close individuals and/or objects. It is preferred that the vibrational energy produced be synchronized to the frequency pulse waves of the processing means.

Thus, as the inputting means plays predetermined acoustic sounds, the processing means of the one or more vibrational units generates frequency pulse waves which cause vibrational energy to be transferred away from the one or more vibrational units.

FIG. 1 illustrates first and second exemplary embodiments 100, 100' of a physical therapy whole sound frequencies device. As shown in FIG. 1, each of the first and second exemplary embodiments 100, 100' of the physical therapy whole sound frequencies device generally comprises a vibrational unit 10, 10', an inputting means 20, and an auditory relay unit 30. The inputting means 20 of both the first and second exemplary embodiments 100, 100' of the physical therapy whole sound frequencies device is in the form of a compact disc (CD) player for playing one or more compact discs 40 comprising predetermined acoustic whole sounds. Also, as illustrated in FIG. 1, it can be seen that the auditory relay unit 30 of both the first and second exemplary embodiments 100, 100' of the physical therapy whole sound frequencies device is in the form of over-ear headphones for delivering audible predetermined acoustic whole sounds to the user. Each of the first and second exemplary embodiments 100, 100' of the physical therapy whole sound frequencies device generally comprises a vibrational unit 10, 10' in the form of a rectangular box. However, the geometry of the vibrational unit 10 used in the first exemplary embodiment 100 of the physical therapy whole sound frequencies device differs from that utilized in the second exemplary embodiment. In particular, as shown in FIG. 1, the vibrational unit 10 of the first exemplary embodiment 100 comprises a shorter length rectangular box as compared to that of the vibrational unit 10' of the second exemplary embodiment 100'. In all other respects, the vibrational units 10, 10' of the first and second exemplary embodiments 100, 100' are generally the same. Namely, each vibrational unit 10, 10' comprises a housing 12, 12' that comprises a plurality of planar sides, wherein oppositely disposed sides are generally parallel to one another, and adjacent sides are generally perpendicular to one another. In one exemplary embodiment, the outer portion of each vibrational unit housing 12, 12' may be formed from a suitable wood material, such as solid maple. Advantageously, the wooden construction of the vibrational unit housing 12, 12' helps the acoustic whole sounds resonate deeply, naturally, and completely (i.e., like a sound box of a guitar). The wooden housing of the vibrational units 10, 10' better conducts the acoustic waves that move through an individual's bones and connective tissue when his or her body is in contact with the vibrational unit 10, 10'.

In an exemplary embodiment, an individual may stand, sit, lay upon, etc. the vibrational unit 10, 10' of the first and second exemplary embodiments 100, 100' of the physical therapy whole sound frequencies device such that the acoustic sound played by the inputting means (i.e., compact disc (CD) player 20) is transferred to be output as vibrational energy through the vibrational unit 10, 10' and through the body of the individual adjacent to and/or substantially close to the vibrational unit 10, 10'. Unlike a typical massage chair, the vibrational units 10, 10' are not in the form of a chair on which the individual lays on in a supine position.

Advantageously, the shapes of the vibrational units 10, 10' represented in FIG. 1 allow for an individual to be in contact with another object that is more fully in contact with the vibrational unit than the individual is. That is, for example, an individual may receive the vibrational energy from the vibrational unit through a chair or wheelchair.

Figure 2:
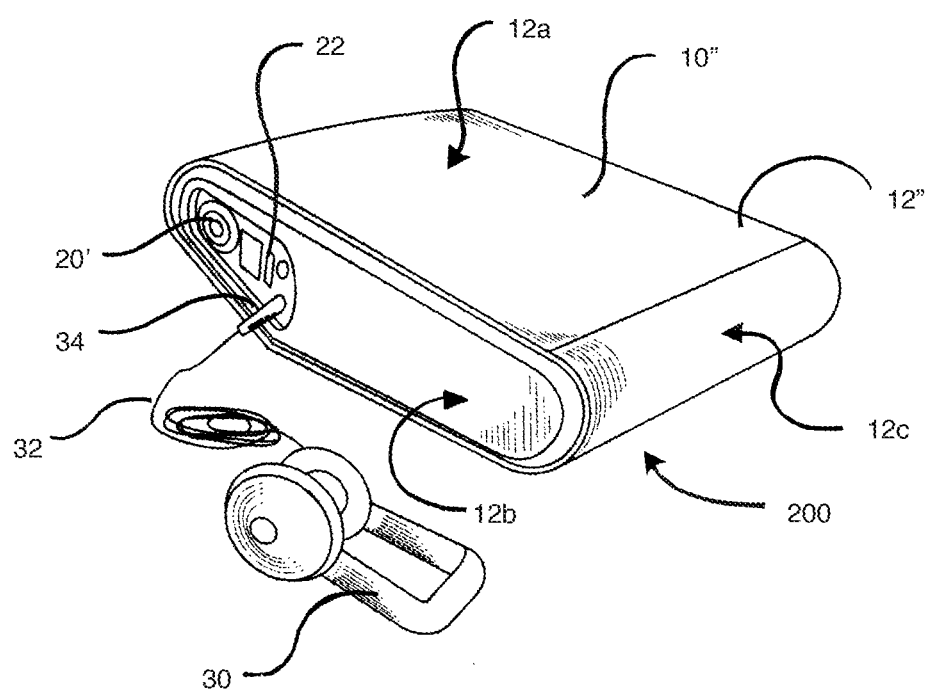
FIG. 2 is a perspective view illustrating a third exemplary embodiment of the physical therapy whole sound frequencies device.

A third exemplary embodiment 200 of a physical therapy whole sound frequencies device is illustrated in FIG. 2. The third exemplary embodiment 200 of the physical therapy whole sound frequencies device illustrated in FIG. 2 is similar in some respects to the first and second exemplary embodiments 100, 100' described above. Like the first and second exemplary embodiments 100, 100' explained above, the third exemplary embodiment 200 of the physical therapy whole sound frequencies device generally comprises a vibrational unit 10", an inputting means 20', and an auditory relay unit 30. As in the first and second exemplary embodiments 100, 100', the auditory relay unit 30 of the third exemplary embodiment 200 of the physical therapy whole sound frequencies device is in the form of over-ear headphones for delivering audible predetermined acoustic whole sounds to the user. However, unlike the first and second exemplary embodiments 100, 100', the inputting means 20' of the third exemplary embodiment 200 comprises a personal digital music player (MP3 player) that is disposed inside the housing 12" of the vibrational unit 10", rather than the externally located compact disc (CD) player described in conjunction with the preceding first and second embodiments. Also, the configuration of the housing 12" of the vibrational unit 10" of the third exemplary embodiment is different than the housings 12, 12' of the vibrational units 10, 10' described above. In particular, as shown in FIG. 2, the vibrational unit 10" of the third exemplary embodiment 200 comprises a housing 12" in the form of a wedge-shaped box. As depicted in FIG. 2, the housing 12" of the vibrational unit 10" comprises a generally planar top surface 12*a* (with a generally planar bottom surface oppositely disposed with respect to surface 12*a*), a generally planar side 12*b* (with another generally planar side surface oppositely disposed with respect to surface 12*b*), and a semi-circular end surface 12*c* (with another semi-circular end surface oppositely disposed with respect to surface 12*c*). In some respects, the vibrational unit 10" of the third exemplary embodiment is shaped such that it has a somewhat triangular cross-sectional area. Similar to the vibrational units 10, 10' described above, the outer housing of the vibrational unit 10" may be formed from a suitable wood material (e.g., maple).

The shape of the vibrational unit 10" of FIG. 2 may be used by an individual on the bottom of the individual's feet, positioned as a lumbar support, placed under an individual's head, positioned adjacent to an individual's neck, etc. to allow for more localized concentration.

Turning again to FIG. 2, it can be seen that the inputting means 20' of the third exemplary embodiment 200 (i.e., the personal digital music player/MP3 player) is recessed-mounted in the side 12*b* of the vibrational unit housing 12". The user interface (i.e., on-off button, sound volume regulation controls, music selection controls, etc.) of the inputting means 20' is integrated into the side 12*b* of the vibrational unit housing 12". In addition, it can be seen that the side 12*b* of the vibrational unit housing 12" is further provided with a universal serial bus (USB) port 22 for operatively connecting the vibrational unit 10" and/or the inputting means 20' to an external digital device, such as a personal computer. Also, adjacent to the USB port 22, the side 12*b* of the vibrational unit housing 12" comprises an electrical outlet/socket for receiving a plug 34 of an electrical cord 32. The electrical cord 32 electrically connects the auditory relay unit 30 (i.e., over-ear headphones) to the inputting means 20' (i.e., the personal digital music player/MP3 player) by means of the vibrational unit 10". Although while a wired connection between the auditory relay unit 30 and the vibrational unit 10"/inputting means 20' is shown in FIG. 2, it is to be understood that the auditory relay unit 30 may alternatively be wirelessly coupled to the vibrational unit 10"/inputting means 20' using a wireless transmitter and corresponding wireless receiver (e.g., the vibrational unit 10"/inputting means 20' may be provided with a wireless transmitter and the auditory relay unit 30 may be provided with a corresponding wireless receiver, or vice versa).

Figure 3B:
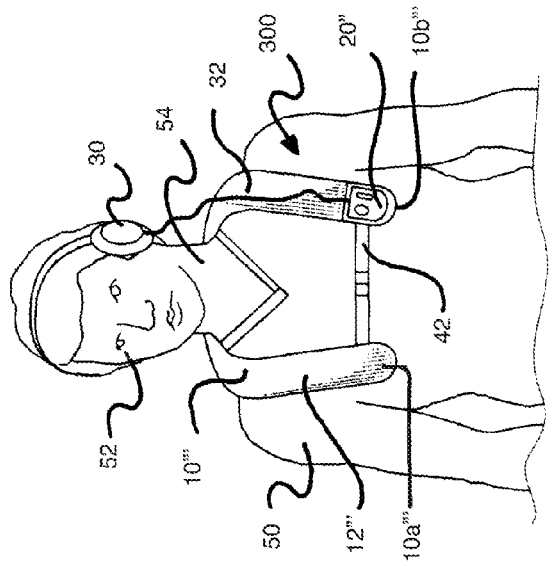
FIG. 3B is a front view illustrating the individual wearing the physical therapy whole sound frequencies device, according to the fourth exemplary embodiment.
Figure 3A:
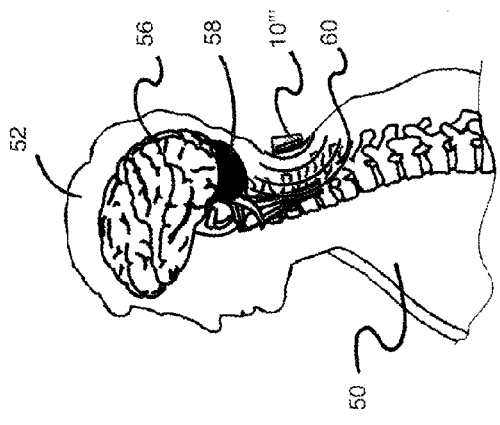
FIG. 3A is a diagrammatic side view illustrating an individual wearing a physical therapy whole sound frequencies device, according to a fourth exemplary embodiment.
Figure 3C:
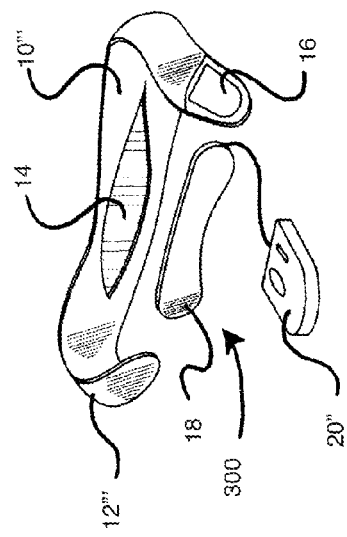
FIG. 3C is a perspective view illustrating the fourth exemplary embodiment of the physical therapy whole sound frequencies device.

A fourth exemplary embodiment 300 of a physical therapy whole sound frequencies device is illustrated in FIGS. 3A-3C. The fourth exemplary embodiment 300 of the physical therapy whole sound frequencies device illustrated in FIGS. 3A-3C is similar in some respects to the first, second, and third exemplary embodiments 100, 100', 200 described above. Like the first, second, and third exemplary embodiments 100, 100', 200 explained above, the fourth exemplary embodiment 300 of the physical therapy whole sound frequencies device generally comprises a vibrational unit 10''', an inputting means 20", and an auditory relay unit 30. As in the first, second, and third exemplary embodiments 100, 100', 200, the auditory relay unit 30 of the fourth exemplary embodiment 300 of the physical therapy whole sound frequencies device is in the form of over-ear headphones for delivering audible predetermined acoustic whole sounds to the user. Also, similar to the third exemplary embodiment 200 described above, the inputting means 20" of the fourth exemplary embodiment 300 comprises a personal digital music player (e.g., MP3 player). However, unlike in the preceding exemplary embodiments 100, 100', 200 described above, the vibrational unit 10''' of the fourth exemplary embodiment 300 is in the form of a wearable scarf-like device that can be placed around the neck and over the shoulders of an individual. In particular, referring to FIG. 3B, it can be seen that the scarf-like vibrational unit 10''' of the fourth exemplary embodiment 300 comprises a generally U-shaped elongated housing 12''' that is worn around the neck 54 of an individual 50, while the auditory relay unit 30 (i.e., over-ear headphones) are worn on the head 52 of the individual 50. As shown in FIG. 3B, in order to maintain the proper positioning on the individual 50, the scarf-like vibrational unit 10''' comprises a first weighted end 10*a*''' and a second weighted end 10*b*'''. In addition, to further retain the scarf-like vibrational unit 10''' in the proper place on the individual, the first and second weighted ends 10*a*''', 10*b*''' may be connected together by a positioning strap 42 utilizing hook-and-loop fasteners.

Next, with reference to FIG. 3C, additional aspects of the fourth exemplary embodiment 300 of the physical therapy whole sound frequencies device will be described. As shown in FIG. 3C, the generally U-shaped elongated housing 12''' of the scarf-like vibrational unit 10''' comprises an elongated slit 14 extending longitudinally therealong for accommodating the vibratory transducer sound plate 18 (i.e., the vibratory transducer sound plate 18 is inserted into the interior of the housing 12''' by means of the elongated slit 14). In addition, the generally U-shaped elongated housing 12''' comprises an aperture 16 disposed therein for accommodating the user interface (i.e., on-off button, sound volume regulation controls, music selection controls, etc.) of the inputting means 20" (i.e., the personal digital music player/MP3 player). The inputting means 20" (i.e., the personal digital music player/MP3 player) is received within the generally U-shaped elongated housing 12''' of the scarf-like vibrational unit 10''', proximate to the second weighted end 10*b*''' thereof. The aperture 16 permits access to the user interface of the internally disposed inputting means 20". In one exemplary embodiment, the outer portion of each vibrational unit housing 12''' may be formed from a cloth material so that it may be comfortably worn around the neck 54 of the individual 50.

Referring again to FIGS. 3B and 3C, it can be seen that the inputting means 20" is operatively coupled to the vibratory transducer sound plate 18 by means of an electrical cord, and similarly, the inputting means 20" is operatively coupled to the auditory relay unit 30 by means of another electrical cord 32 (see FIG. 3B). Although, as described above for the third exemplary embodiment 200, while wired connections between the auditory relay unit 30 and the vibratory transducer sound plate 18 and the inputting means 20" are shown in FIGS. 3B and 3C, it is to be understood that the auditory relay unit 30 may alternatively be wirelessly coupled to the inputting means 20" using a wireless transmitter and corresponding wireless receiver, and similarly, the vibratory transducer sound plate 18 may alternatively be wirelessly coupled to the inputting means 20" using a wireless transmitter and corresponding wireless receiver.

In one or more embodiments, the inputting means 20" (i.e., the personal digital music player/MP3 player) of FIGS. 3B and 3C additionally comprises an amplifier disposed inside the housing thereof for increasing the power level (i.e., amplitude) of the signal from the inputting means 20". The inputting means 20" and amplifier may additionally comprise a power source (e.g., one or more batteries) disposed therein for providing power to the physical therapy whole sound frequencies device.

Now, with reference to FIGS. 3A and 3B, the functionality of the fourth exemplary embodiment 300 of the physical therapy whole sound frequencies device will be described. As shown in FIG. 3A, because the scarf-like vibrational unit 10''' is positioned against the neck 54 of the individual 50, the acoustic whole sounds are transferred through the spinal cord 60 to the entire body of the individual 50. The acoustic whole sounds also create an acoustic wave within the cerebrospinal fluid (CSF), thereby stimulating the ventricles and cerebellum 58 of the individual's brain 56, and additionally disseminating stem cells. The scarf-like vibrational unit 10''' activates the sensory motor cortex of the individual's brain 56 and vibrates the cerebrospinal fluid (CSF) so as to trigger neurogenesis. The auditory relay unit 30 in the form of over-ear headphones activates the auditory cortex and cerebellum 58 of the individual's brain 56. As such, by virtue of the biological processes produced thereby, the physical therapy whole sound frequencies device advantageously relaxes the body of the individual 50 and lessens or stops pain. The physical therapy whole sound frequencies device stimulates cerebrospinal fluid (CSF) flow in order to "clean" the brain 56 of the individual 50, facilitate the distribution of hormones, and facilitate the dissemination of stem cells.

FIG. 4 is a side view illustrating an individual 50' utilizing the physical therapy whole sound frequencies device 200 in a seated position. In FIG. 4, the individual 50' is seated in a chair 64 with her hands disposed on the keyboard 68, which is supported on a desktop 70. In other words, FIG. 4 depicts a typical position of a user seated at a desk, and typing on a computer (i.e., a common office scenario). As shown in this figure, the wedge-shaped housing 12" of the vibrational unit 10" is disposed underneath the bottom of the individual's feet 62. More particularly, the individual places each of her feet 62 on the sloped top surface 12a of the vibrational unit housing 12". In FIG. 4, the vibrational unit 10" of the physical therapy whole sound frequencies device 200 is disposed proximate to the base 66 of the chair 64. Referring again to FIG. 4, it can be seen that the auditory relay unit 30 (i.e., over-ear headphones) are disposed on the head 52' of the individual 50.

Now, with reference to FIG. 4, the functionality of the second exemplary embodiment 200 of the physical therapy whole sound frequencies device will be described. As shown in FIG. 4, because the wedge-shaped housing 12" of the vibrational unit 10" is disposed underneath the feet 62 of the individual 50', the acoustic whole sounds are conducted through the long bones of the individual's legs to the rest of her body. The auditory relay unit 30 in the form of over-ear headphones activates the auditory cortex and cerebellum of the individual's brain. As such, by virtue of the biological processes produced thereby, the physical therapy whole sound frequencies device 200 advantageously relaxes the body of the individual 50' and lessens or stops pain. The physical therapy whole sound frequencies device 200 stimulates cerebrospinal fluid (CSF) flow in order to "clean" the brain of the individual 50', facilitate the distribution of hormones, and facilitate the dissemination of stem cells.

Figure 5:
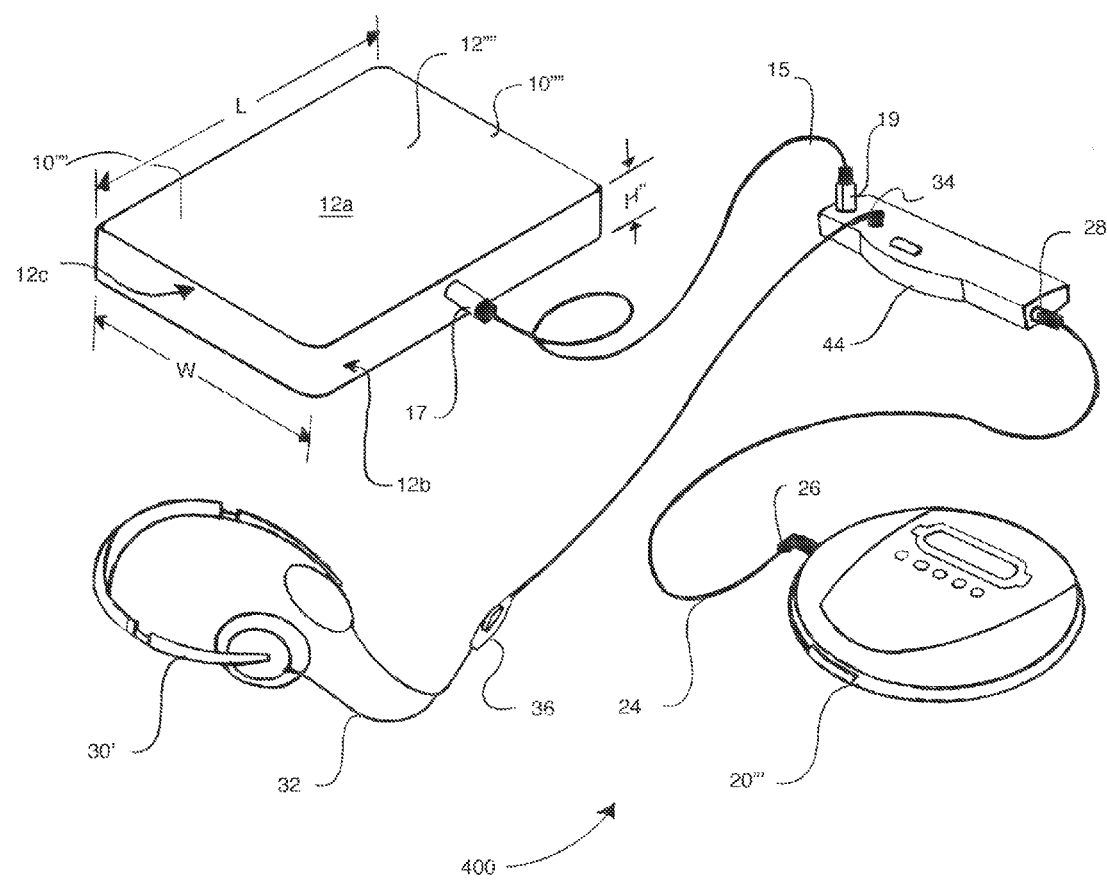
FIG. 5 is a perspective view illustrating a fifth exemplary embodiment of the physical therapy whole sound frequencies device.

A fifth exemplary embodiment 400 of a physical therapy whole sound frequencies device is illustrated in FIG. 5. The fifth exemplary embodiment 400 of the physical therapy whole sound frequencies device illustrated in FIG. 5 is similar in some respects to the first, second, and third exemplary embodiments 100, 100', 200 described above. Like the first, second, and third exemplary embodiments 100, 100', 200 explained above, the fifth exemplary embodiment 400 of the physical therapy whole sound frequencies device generally comprises a vibrational unit 10"", an inputting means 20''', and an auditory relay unit 30'. Similar to the first and second exemplary embodiments 100, 100', the vibrational unit 10"" of the physical therapy whole sound frequencies device 400 is in the form of a rectangular sound box. Also, the geometry of the housing 12"" of the vibrational unit 10"" is similar to that of vibrational units 10, 10' in that the housing 12"" comprises a plurality of planar sides, wherein oppositely disposed sides are generally parallel to one another, and adjacent sides are generally perpendicular to one another. In particular, as shown in FIG. 5, the housing 12"" of the vibrational unit 10"" comprises a generally planar top surface 12a (with a generally planar bottom surface oppositely disposed with respect to surface 12a), a generally planar side surface 12b (with another generally planar side surface oppositely disposed with respect to surface 12b), and a generally planar end surface 12c (with another generally planar end surface oppositely disposed with respect to surface 12c). Similar to the vibrational units 10, 10', 10" described above, the outer housing of the vibrational unit 10"" may be formed from a suitable wood material (e.g., solid maple).

As described above for the vibrational unit 10" of FIG. 2, the vibrational unit 10"" of FIG. 5 may be used by an individual on the bottom of the individual's feet, positioned as a lumbar support, placed under an individual's head, positioned adjacent to an individual's neck, etc. to allow for more localized concentration.

In an exemplary embodiment, the housing 12"" of the vibrational unit 10"" has an overall length L of approximately 11.0 inches, a width W of approximately 9.0 inches, and a height of H approximately 1.5 inches. Although, it is to be understood that the invention is in no way limited to these particular dimensions. Rather, the invention may be practiced using any other suitable dimensions without departing from the spirit and scope of the appended claims.

In one or more embodiments, the physical therapy whole sound frequencies device 400 is designed to be portable and used in a variety of home, institutional, and office environments. As such, in these one or more embodiments, the shape and sizes are selected based upon ergonomic, transportation and usage requirements. For example, considering the ergonomic requirements, a maximum thickness of 1.5 inches is desirable so that the vibrational unit 10"" is capable of being single handedly grasped, lifted and carried by a typical female. This same maximum dimension allows the unit to be placed comfortably between a person and furniture. The minimum width and length dimensions of approximately 9.0 inches by approximately 11.0 inches enables all 50th percentile males and 75th percentile females to place their feet effortlessly and comfortably upon the vibrational unit 10"" while seated, supine or standing.

Referring again to FIG. 5, as in the first and second exemplary embodiments 100, 100', the inputting means 20''' of the fifth exemplary embodiment 400 of the physical therapy whole sound frequencies device is in the form of a compact disc (CD) player for playing one or more compact discs comprising predetermined acoustic whole sounds. Rather than the rectangular housing of the inputting means 20 in FIG. 1, the inputting means 20''' (i.e., compact disc (CD) player) of FIG. 5 has a generally circular shape. In addition, as shown in FIG. 5, similar to the preceding exemplary embodiments 100, 100', 200, 300 of the physical therapy whole sound frequencies device, the auditory relay unit 30' of the fifth exemplary embodiment 400 is in the form of headphones (either over-ear type or non-over-ear type) for delivering audible predetermined acoustic whole sounds to the user. However, unlike the exemplary embodiments 100, 100', 200, 300 described above, the fifth embodiment 400 of the physical therapy whole sound frequencies device comprises a separate battery-powered amplifier unit 44 for increasing the power level (i.e., amplitude) of the signal from the inputting means 20'''. In an exemplary embodiment, the amplifier unit 44 comprises two AA-size batteries disposed therein for providing power to the physical therapy whole sound frequencies device 400.

With continued reference to FIG. 5, it can be seen that the battery-powered amplifier unit 44 may be electrically connected to the vibrational unit 10'''' by an electrical cord 15. That is, an electrical plug 17 at a first end of the electrical cord 15 plugs into an electrical socket/outlet on the side 12b of the vibrational unit housing 12''', and an electrical plug 19 at a second, opposite end of the electrical cord 15 plugs into an electrical socket/outlet on the top of the amplifier unit 44. Similarly, the battery-powered amplifier unit 44 may be electrically connected to the inputting means 20''' by an electrical cord 24. Specifically, an electrical plug 26 at a first end of the electrical cord 24 plugs into an electrical socket/outlet on the circular sidewall of the housing of the inputting means 20''', and an electrical plug 28 at a second, opposite end of the electrical cord 24 plugs into an electrical socket/outlet on the one longitudinal end of the amplifier unit 44. Finally, the battery-powered amplifier unit 44 may be electrically connected to the auditory relay unit 30' (i.e., headphones) by an electrical cord 32. In particular, an electrical plug 34 at an end of the electrical cord 32, which is opposite to the headphones, plugs into an electrical socket/outlet on the top of the amplifier unit 44, proximate to the electrical plug 19 outlet location. As shown in FIG. 5, the electrical cord 32 of the auditory relay unit 30' may additionally comprise a volume control module 36 disposed thereon (e.g., with a rotatable volume control wheel) for regulating the volume of the auditory relay unit 30' (i.e., headphones). Although while a wired connection between the amplifier unit 44 and each of the vibrational unit 10'''', inputting means 20''', and auditory relay unit 30' is shown in FIG. 5, it is to be understood that the amplifier unit 44 may alternatively be wirelessly coupled to the each of these constituent components 10'''', 20''', and 30' of the physical therapy whole sound frequencies device 400 using a wireless transmitter and corresponding wireless receiver (e.g., the amplifier unit 44 may be provided with a wireless transmitter(s) and each of the components 10'''', 20''', and 30' may be provided with a corresponding wireless receiver(s), or vice versa).

Figure 6:
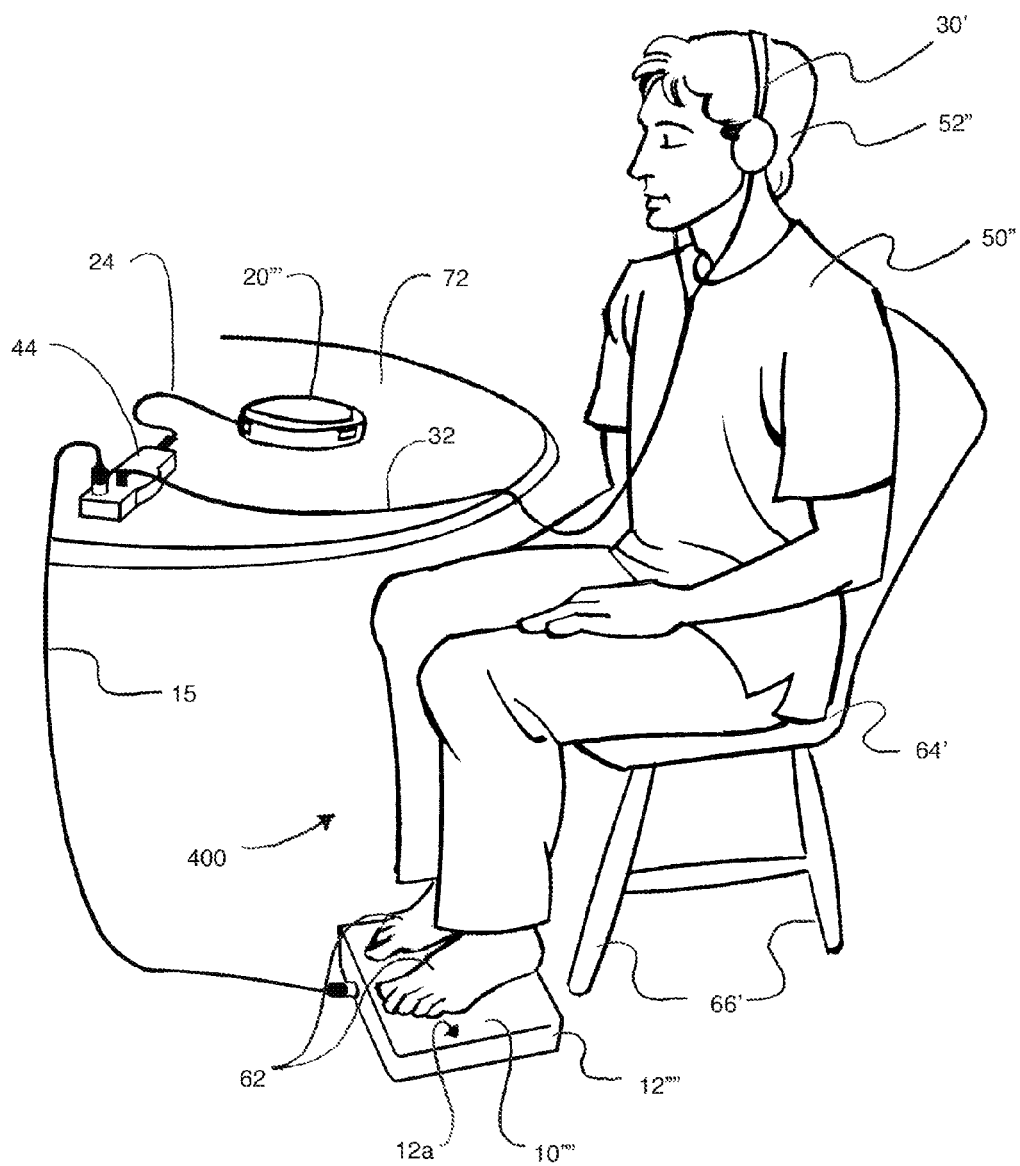
FIG. 6 is a perspective view illustrating an individual utilizing the fifth exemplary embodiment of the physical therapy whole sound frequencies device.

FIG. 6 is a perspective view illustrating an individual 50" utilizing the physical therapy whole sound frequencies device 400 in a seated position. In FIG. 6, the individual 50" is seated in a chair 64' in a relaxed position with his hands generally placed in his lap. In other words, FIG. 6 depicts a typical position of a user seated at a table 72. As shown in this figure, the rectangular box-shaped housing 12'''' of the vibrational unit 10'''' is disposed underneath the bottom of the individual's feet 62. More particularly, the individual 50" places each of his feet 62 on the generally planar top surface 12a of the vibrational unit housing 12''''. In FIG. 6, the vibrational unit 10'''' of the physical therapy whole sound frequencies device 400 is disposed proximate to the base 66' of the chair 64'. Referring again to FIG. 6, it can be seen that the auditory relay unit 30' (i.e., over-ear headphones) are disposed on the head 52" of the individual 50". Also, as illustrated in FIG. 6, the inputting means 20''' (i.e., compact disc (CD) player) and the amplifier unit 44 are conveniently supported on the top of the table 72.

Now, with continued reference to FIG. 6, the functionality of the fifth exemplary embodiment 400 of the physical therapy whole sound frequencies device will be explained. As shown in FIG. 6, because the rectangular box-shaped housing 12'''' of the vibrational unit 10'''' is disposed underneath the feet 62 of the individual 50", the acoustic whole sounds are conducted through the long bones of the individual's legs to the rest of his body. The auditory relay unit 30' in the form of over-ear headphones activates the auditory cortex and cerebellum of the individual's brain. As such, by virtue of the biological processes produced thereby, the physical therapy whole sound frequencies device 400 advantageously relaxes the body of the individual 50" and lessens or stops pain. The physical therapy whole sound frequencies device 400 stimulates cerebrospinal fluid (CSF) flow in order to "clean" the brain of the individual 50", facilitate the distribution of hormones, and facilitate the dissemination of stem cells.

The illustrated vibrational units 10, 10', 10", 10''', 10'''' may be used in combination with one another or singly. Further, it should be understood that the vibrational units 10, 10', 10", 10''', 10'''' illustrated in the drawings are representative and do not include all possible variations of the vibrational units 10, 10', 10", 10''', 10''''.

As explained above, the device of the present invention further includes one or more auditory relay units 30, 30' for conveying the acoustic sounds of the inputting means. Thus, the auditory relay unit may be in the form of, for example, auditory speakers, headphones, or a combination thereof. It is preferred that the auditory relay unit be in the form of headphones that substantially cover both ears of an individual in order to substantially reduce the possible pollution of the predetermined acoustic sound from the inputting means.

As illustrated in FIGS. 4 and 6, an individual positions himself or herself in substantial physical contact with one or more vibrational units of the present device. In FIGS. 4 and 6, the individual is contacting his or her feet against a vibrational unit connected to an inputting means. In addition, the individual has placed the auditory relay unit, in the form of headphones, over his or her ears.

Once in a comfortable position with both the vibrational unit and the auditory relay unit, the inputting means is powered to play predetermined acoustic sound. The acoustic sound from the inputting means is processed into vibrations emitted by the vibrational unit against the soles of the individual's feet such that the vibrations are synchronized to the acoustic sound of the inputting means. Simultaneously, the individual is listening to the acoustic sound through the headphones.

The synchronized sound and vibrational energy is able to synergistically promote positive cell activity in order to relieve pain, cause relaxation, reduce stress, relieve sinus and tension pain, tone tissues, promote muscle development, improve mood, promote sleep, improve circulation, and improve neural functions.

The vibrational energy and sound passes through the entire organism by way of an individual's skeleton, the extra-cellular matrix of connective fibrous tissue, and through auditory waves within the fluids of the circulatory system and/or central nervous system.

Together, the vibrational energy and the sound stimulate both hemispheres of an individual's brain; a hemispheric synchronization is achieved thereby bringing both body and mind into a harmony.

In various exemplary embodiments, the device may be connected to one or more computers for analyzing and/or monitoring physiological status of an individual.

Figure 7:
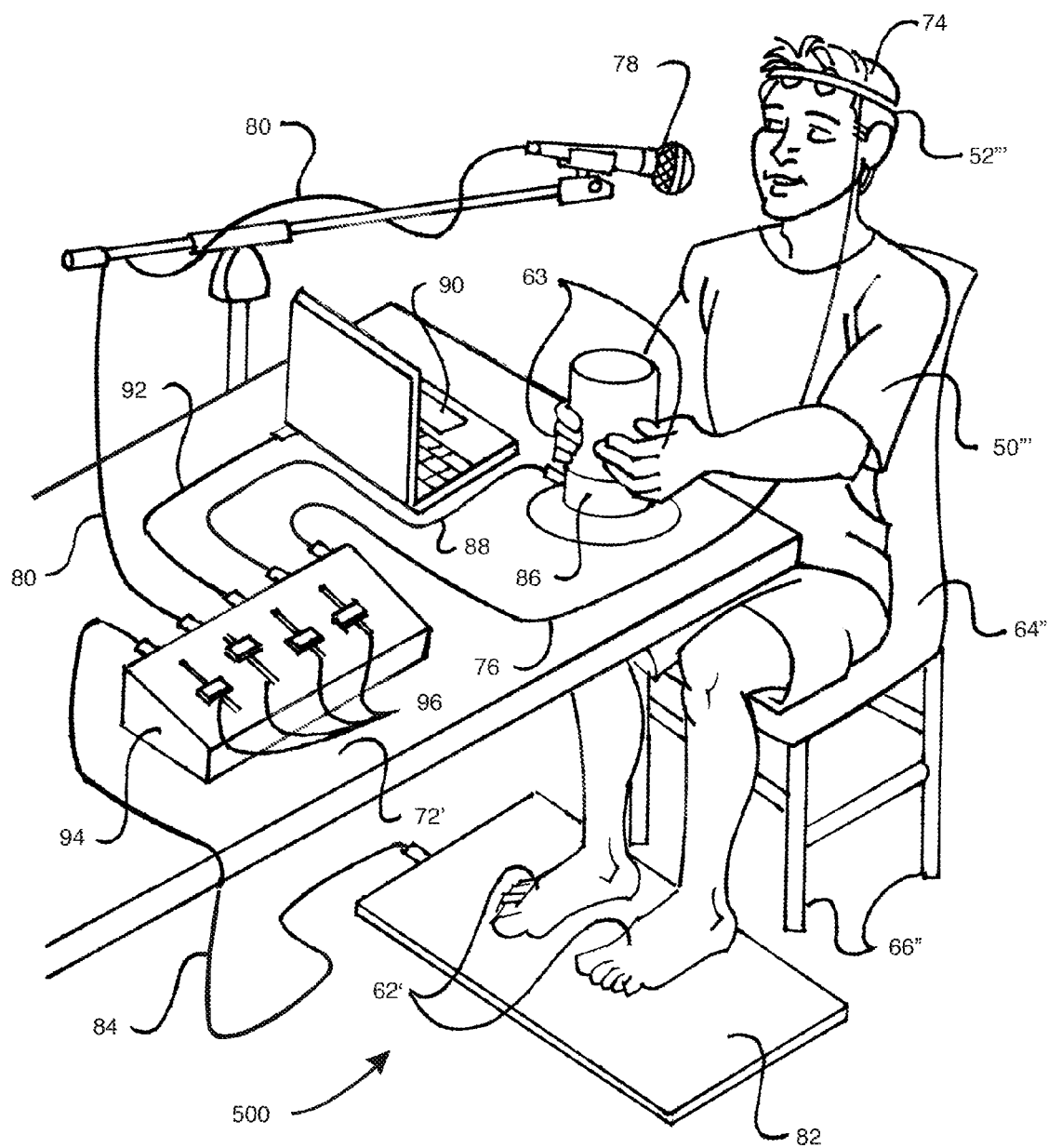
FIG. 7 is a perspective view illustrating an exemplary embodiment of a recording system used to record the acoustic whole sounds that are utilized in the embodiments of the physical therapy whole sound frequencies device described herein.

An exemplary embodiment of a recording system 500, which is used to record the acoustic whole sounds utilized in the embodiments 100, 100', 200, 300, 400 of the physical therapy whole sound frequencies device, is illustrated in FIG. 7. In FIG. 7, the recording subject 50''' is seated in a chair 64'' with his feet 62' disposed on the top surface of footplate transducer device 82, and his hands 63 disposed around a cylindrical input transducer device 86. In addition, the recording subject 50''' is provided with a headband device 74 disposed around his head 52''', and a microphone input device 78 disposed proximate to the mouth of the recording subject 50'''. As shown in FIG. 7, the footplate transducer device 82 of the recording system 500 is disposed proximate to the base and legs 66'' of the chair 64''. Referring again to FIG. 7, it can be seen that the cylindrical input transducer device 86, a laptop computing device 90, and an input mixer device 94 are supported on the top of the table 72'. While not explicitly shown in FIG. 7, it is to be understood that the recording subject 50''' may also be provided with headphones on his head 52''' for feedback purposes during the recording of the acoustic whole sounds. That is, the headphones would provide the recording subject 50''' with a means of quasi real-time feedback so that he could make desired adjustments to the recorded acoustic whole sounds during the recording process (e.g., he could adjust the input devices 82, 86, tweak frequencies, etc).

In the recording setup of FIG. 7, the microphone input device 78 is used to record the vocalized sound waves from the lungs of the recording subject 50''' (i.e., the vocalized pathway), the headband device 74 is used to record sound waves emanating from the head 52''' of the recording subject 50''', the footplate transducer device 82 is used to record the sound waves conducted through the feet 62' of the recording subject 50''', and the cylindrical input transducer device 86 is used to record the sound waves conducted through the hands 63 of the recording subject 50'''. In one exemplary embodiment, the cylindrical input transducer device 86 may comprise one or more microphones surrounded by a cylindrical housing in order to maximize the finger surface area of the recording subject 50''' that is in contact with the cylindrical input transducer device 86. Advantageously, because the exemplary recording system 500 of FIG. 7 captures sound waves from virtually all major portions of the individual's body, it is possible to record a comprehensive plurality of message templates from virtually all of the individual's body. As such, the recording system 500 is capable of comprehensively capturing the cell messages produced by the body of the recording subject 50''' so that these cell messages can be recorded on a medium (e.g., a compact disc (CD)) that is utilized in the physical therapy whole sound frequencies devices described above.

With continued reference to FIG. 7, the hardware architecture of the recording system 500 will be further described. In FIG. 7, it can be seen that the headband device 74 may be electrically connected to the input mixer device 94 by an electrical cord 76, while the microphone input device 78 may be electrically connected to the input mixer device 94 by an electrical cord 80. Similarly, the footplate transducer device 82 may be electrically connected to the input mixer device 94 by an electrical cord 84, while the cylindrical input transducer device 86 may be electrically connected to the input mixer device 94 by an electrical cord 88. Also, as shown in FIG. 7, the laptop computing device 90 may be electrically connected to the input mixer device 94 by an electrical cord 92. As such, the operative coupling of all the input devices 74, 78, 82, 86 to the input mixer device 94 and the laptop computing device 90 enables the myriad of sound waves recorded from the devices 74, 78, 82, 86 to be appropriately mixed and refined by the recording subject 50''', and then recorded on a recording medium (e.g., a compact disc (CD)) using the laptop computing device 90. As shown in FIG. 7, the input mixer device 94 is provided with a plurality of adjustable control levers 96 disposed thereon for adjusting output signals from each of the recording devices 74, 78, 82, 86 (e.g., by adjusting the amplitude of the signals, etc.).

The acoustic whole sounds that are recorded directly from the body of the recording subject 52''' by the recording system 500, and then subsequently encoded on the media (e.g., compact discs (CD), non-volatile memory) that is utilized in the embodiments 100, 100', 200, 300, 400 of the physical therapy whole sound frequencies devices described herein, comprise harmonic sound content with a root frequency, a plurality of overtone frequencies that are greater than the root frequency and mathematically proportional to the root frequency, and a plurality of undertone frequencies that are less than the root frequency and mathematically proportional to the root frequency. The plurality of overtone frequencies and the plurality of undertone frequencies of the harmonic sound content are identical or substantially identical to the proportional harmonic frequencies of body cells and/or molecules because they are recorded directly from the human body (i.e., of the recording subject 52'''). That is, the acoustic whole sounds recorded by the system 500, and then subsequently used in the devices 100, 100', 200, 300, 400, comprise natural whole acoustic harmonics from a natural cellular source. The system 500 records directive acoustic cell sounds from the body of the recording subject 52'''.

In addition, the acoustic whole sounds that are recorded directly from the body of the recording subject 50''' by the recording system 500, and then subsequently encoded on the media (e.g., compact discs (CDs), non-volatile electronic storage media, etc.) that is utilized in the embodiments 100, 100', 200, 300, 400 of the physical therapy whole sound frequencies device described herein, comprise a plurality of message templates. Each of the plurality of message templates includes harmonic sound content recorded from the body of the recording subject 52''' that is specially recorded and produced so as to have a predetermined targeted effect on tissues and cells of human beings when using the physical therapy whole sound frequencies devices. In order to produce the message templates, the recording subject 50''', through voluntary action, directs cellular material in his body to execute a specific biological function (e.g., dilate lung tissue, or gate pain receptors). The message creation process and the action of the biological tissue happens near simultaneously. Thus, both actions are recorded on the reording media by the recording system 500.

During the recording process, the recording subject 50''' is able to control the content of the message templates recorded by the system 500 by pressure manipulations of his larynx, which contain chemo-neuroreceptors and mechano-neuroreceptors of the tenth cranial nerve (vagus nerve) and the parasympathetic nervous system, which enervates the entire organ system of his body. The dissemination of the message moves outward into efferent and afferent nerves, which means they head upward to the Nucleus Tratus Solitari (NTS) of the medulla oblongata into the Reticular Formation of the brainstem and downward into the targeted organs themselves. The Reticular Formation of the body has the final control over the manner in which the request will be executed, and it directs the action from the brain downward through the vagus nerve and spinal cord. Air passing over the pressure shaped larynx carries the acoustic message "vocally" to the recording device. A recording then includes acoustic patterns of: the shaping of the message within the larynx, the neurological interpretation of the message to the NTS, the reticular commands to the organ system, and then the response of the organs themselves. This combination of acoustic message patterns becomes a "message template" for cells "listening" to the recordings through the previously described embodiments of the device, to execute those same patterns within the body of the listening subject. Each post-produced recording can contain multiple message templates, mixed to be played simultaneously or sequentially, to multiple tissue targets, in-order to create a total systemic response to the therapy.

Further, the acoustic whole sounds that are recorded directly from the body of the recording subject 50''' by the recording system 500, and then subsequently encoded on the media (e.g., compact discs (CDs)), non-volatile electronic storage media, etc.) that is utilized in the embodiments 100, 100', 200, 300, 400 of the physical therapy whole sound frequencies device described herein, comprise a plurality of infrasonic message templates with sub-audible frequency content. When using the physical therapy whole sound frequencies device described herein, the plurality of infrasonic message templates are directly transmitted to the individual's body using the one or more vibrational units 10, 10', 10", 10''', 10'''', and the plurality of infrasonic message templates are indirectly transmitted to the individual's body using the auditory relay unit 30, 30'. These infrasonic message templates are directly expressed in the undertone frequency content of the acoustic whole sounds delivered by the physical therapy whole sound frequencies device, namely the one or more vibrational units 10, 10', 10", 10''', 10''''. As such, the physical therapy whole sound frequencies device described herein provides a message-templated acoustic whole sound in a form in which the individual's body will respond and heal. The acoustic whole sound delivered by the physical therapy whole sound frequencies device comprises a complete whole harmonic sound that includes both vocal expressions and infrasonic transduction simultaneously recorded by the recording subject 50''' using the recording system 500. The transducers of the input devices 74, 82, 86 record the infrasonic expressions produced by the body, while the microphone input device 78 of the recording system 500 records the vocal expression of the recording subject 50'''. The post-recording technology of the recording system 500, namely that afforded by the laptop computing device 90 and the input mixer device 94, enables the recording subject 50''' to loop, layer, and overlap a message template so the desired effect on the individual using the physical therapy whole sound frequencies device may be achieved. That is, the technology of the recording system 500 enables multiple body systems and multiple problems to be addressed at the same time.

For example, a local muscle skeletal back problem creates spasms, bracing, pain, anxiety and fear. Some of these problems are "local" issues, namely spasms and bracing. Although, others are more global: pain, anxiety, fear and secondarily muscle accommodation to the injury. To treat this incident we have to address both local and global issues. Muscle relaxation and elongation message templates address the spasms, bracing and their local pain as well as secondary accommodations. Neural calming message template patterns are directed at the brain stem to "gate" pain receptors and placate anxiety. Neural excitation patterns are directed to other brain regions that will release dopamine and other endorphins. In this case, the injury is not "cured." The body's global and local responses to the injury are managed and balanced to eliminate nearly all discomfort during the acute phase and aid and stimulate the healing phases without the performance reducing chemical side effects of potent pharmaceuticals. A recording developed by the recording system 500, and utilized in the embodiments 100, 100', 200, 300, 400 of the physical therapy whole sound frequencies device, may contain ten or more different message templates to address all the issues of a global body response to a stressor, impairment or disease.

The delivery system utilized by the embodiments 100, 100', 200, 300, 400 of the physical therapy whole sound frequencies device ensures that infrasonic message templates are transducted through the bones and body connective tissue via the vibrational units 10, 10', 10", 10''', 10'''' (i.e., sound boxes) and auditory relay units 30, 30' (i.e., headphone transducers). The vocalized messages heard through the auditory relay units 30, 30' are conducted and processed through the nervous system of the individual, and then converted to infrasonic sound and transducted by the perineural connective tissue to the targeted cell systems.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A device for relaxing and promoting healing of biological tissue, the device comprising:
   an inputting means configured to generate a digital signal based upon one or more predetermined acoustic whole sounds from a non-transitory computer readable media introduced to the inputting means;
   the non-transitory computer readable media configured to be introduced into the inputting means, wherein said non-transitory computer readable media comprises the one or more predetermined acoustic whole sounds, the one or more predetermined acoustic whole sounds comprising harmonic sound content with a root frequency, a plurality of overtone frequencies that are greater than the root frequency and mathematically proportional to the root frequency, and a plurality of undertone frequencies that are less than the root frequency and mathematically proportional to the root frequency, wherein at least one of the plurality of overtone frequencies and the plurality of undertone frequencies of the harmonic sound content is substantially identical to the proportional harmonic frequencies of body cells and/or molecules such that the one or more predetermined acoustic whole sounds are configured to engage and direct the body cells and/or molecules of human beings through the harmonic sound content;

one or more vibrational units connected to the inputting means, the one or more vibrational units having:
a processing device configured to generate frequency pulse waves based upon the digital signal relayed by the connected inputting means; and
one or more transducers configured to vibrate the one or more vibrational units using the one or more predetermined acoustic whole sounds introduced to the inputting means effective to transfer the one or more predetermined acoustic whole sounds into one or more of bones, tissues or peripheral nerves of an individual; and at least one auditory relay unit connected to the inputting means, the at least one auditory relay unit having speakers for transferring an auditory signal associated with the digital signal of the inputting means;

wherein the one or more vibrational units and the at least one auditory relay unit are configured to be placed in contact with the individual for a predetermined period of time.

2. The device according to claim 1, wherein the inputting means comprises one of: (i) a personal digital music player, (ii) a compact disc (CD) player, (iii) a digital video disc (DVD) player, (iv) a smartphone, (v) a digital tablet device, and (vi) a personal computing device.

3. The device according to claim 1, wherein the inputting means is external to the one or more vibrational units, and wherein the inputting means is operatively coupled to the one or more vibrational units by means of one or more electrical cords or a wireless connection.

4. The device according to claim 1, wherein the inputting means is disposed inside a housing of the one or more vibrational units.

5. The device according to claim 1, wherein the one or more vibrational units comprise a housing, the housing of each of the one or more vibrational units being in the shape of either a generally rectangular box or a generally wedge-shaped box configured to be disposed underneath a portion of a body of the individual.

6. The device according to claim 1, wherein the at least one auditory relay unit comprises one of: (i) a pair of audio headphones, (ii) a pair of audio speakers, and (iii) a combination of audio headphones and audio speakers.

7. The device according to claim 1, wherein the one or more predetermined acoustic whole sounds introduced to the inputting means further comprise a plurality of message templates, each of the plurality of message templates comprising harmonic sound content configured to have a predetermined targeted effect on tissues and cells of human beings.

8. The device according to claim 7, wherein the plurality of message templates of the one or more predetermined acoustic whole sounds comprise one or more infrasonic message templates; and wherein the at least one auditory relay unit is configured to indirectly transmit the one or more infrasonic message templates to a first portion of the individual's body and the one or more vibrational units are configured to directly transmit the one or more infrasonic message templates to a second portion of the individual's body.

9. A method for relaxing and promoting healing of biological tissue, the method comprising the steps of:
positioning a device adjacent to an individual's body, the device comprising:
an inputting means configured to generate a digital signal based upon one or more predetermined acoustic whole sounds introduced to the inputting means, the one or more predetermined acoustic whole sounds comprising harmonic sound content with a root frequency, a plurality of overtone frequencies that are greater than the root frequency and mathematically proportional to the root frequency, and a plurality of undertone frequencies that are less than the root frequency and mathematically proportional to the root frequency, wherein at least one of the plurality of overtone frequencies and the plurality of undertone frequencies of the harmonic sound content is substantially identical to the proportional harmonic frequencies of body cells and/or molecules such that the one or more predetermined acoustic whole sounds are configured to engage and direct the body cells and/or molecules of human beings through the harmonic sound content;
one or more vibrational units connected to the inputting means, the one or more vibrational units configured to produce vibration, the one or more vibrational units using sound to perform the vibration, and the one or more vibrational units having:
a processing device configured to generate frequency pulse waves based upon the digital signal relayed by the connected inputting means; and
one or more transducers configured to vibrate the one or more vibrational units using the one or more predetermined acoustic whole sounds introduced to the inputting means effective to transfer the one or more predetermined acoustic whole sounds into one or more of bones, tissues or peripheral nerves of an individual; and
at least one auditory relay unit connected to the inputting means, the at least one auditory relay unit having speakers for transferring an auditory signal associated with the digital signal of the inputting means;
positioning the at least one auditory relay unit proximate to, or on a first portion of the individual's body;
positioning the one or more vibrational units proximate to, or in contact with a second portion of the individual's body;
introducing the one or more predetermined acoustic whole sounds to the inputting means; and
transmitting the one or more predetermined acoustic whole sounds to the first and second portions of the individual's body for a predetermined period of time using the at least one auditory relay unit and the one or more vibrational units.

10. The method according to claim 9, wherein the step of positioning the at least one auditory relay unit comprises positioning the at least one auditory relay unit on a head of the individual's body.

11. The method according to claim 10, wherein the step of positioning the one or more vibrational units comprises positioning the one or more vibrational units adjacent to one or more limbs of the individual's body.

12. The method according to claim 9, wherein the step of positioning the at least one auditory relay unit comprises positioning the at least one auditory relay unit at a first end of the individual's body, and wherein the step of positioning the one or more vibrational units comprises positioning the one or more vibrational units at a second end of the individual's body, the first end of the individual's body being disposed generally opposite to the second end of the individual's body.

13. A method for relaxing and promoting healing of biological tissue, the method comprising the steps of:
   positioning a device adjacent to an individual's body, the device comprising:
      an inputting means configured to generate a digital signal based upon one or more predetermined acoustic whole sounds introduced to the inputting means, the one or more predetermined acoustic whole sounds including proportional harmonic overtone frequencies and a plurality of message templates, each of the plurality of message templates comprising harmonic sound content configured to have a predetermined targeted effect on tissues and cells of human beings, and the plurality of message templates of the one or more predetermined acoustic whole sounds comprising one or more infrasonic message templates;
      one or more vibrational units connected to the inputting means, the one or more vibrational units configured to produce vibration, the one or more vibrational units using sound to perform the vibration, and the one or more vibrational units having:
         a processing device configured to generate frequency pulse waves based upon the digital signal relayed by the connected inputting means; and
         one or more transducers configured to vibrate the one or more vibrational units using the one or more predetermined acoustic whole sounds introduced to the inputting means effective to transfer the one or more predetermined acoustic whole sounds into one or more of bones, tissues or peripheral nerves of an individual; and
      at least one auditory relay unit connected to the inputting means, the at least one auditory relay unit having speakers for transferring an auditory signal associated with the digital signal of the inputting means;
   positioning the at least one auditory relay unit proximate to, or on a first portion of the individual's body;
   positioning the one or more vibrational units proximate to, or in contact with a second portion of the individual's body;
   introducing the one or more predetermined acoustic whole sounds to the inputting means; and
   transmitting the one or more predetermined acoustic whole sounds to the first and second portions of the individual's body for a predetermined period of time using the at least one auditory relay unit and the one or more vibrational units, and wherein transmitting the one or more predetermined acoustic whole sounds to the first and second portions of the individual's body further comprises directly transmitting the one or more infrasonic message templates to the second portion of the individual's body using the one or more vibrational units, and indirectly transmitting the one or more infrasonic message templates to the first portion of the individual's body using the at least one auditory relay unit.

14. The method according to claim 13, wherein the one or more predetermined acoustic whole sounds further comprise harmonic sound content with a root frequency, a plurality of overtone frequencies that are greater than the root frequency and mathematically proportional to the root frequency, and a plurality of undertone frequencies that are less than the root frequency and mathematically proportional to the root frequency, and wherein at least one of the plurality of overtone frequencies and the plurality of undertone frequencies of the harmonic sound content is substantially identical to the proportional harmonic frequencies of body cells and/or molecules; and
   wherein the step of transmitting the one or more predetermined acoustic whole sounds further comprises transmitting the one or more predetermined acoustic whole sounds to the individual's body so as to engage and direct the body cells and/or molecules of the individual through the harmonic sound content.

15. The method according to claim 13, wherein the step of positioning the at least one auditory relay unit comprises positioning the at least one auditory relay unit on a head of the individual's body.

16. The method according to claim 15, wherein the step of positioning the one or more vibrational units comprises positioning the one or more vibrational units adjacent to one or more limbs of the individual's body.

17. The method according to claim 13, wherein the step of positioning the at least one auditory relay unit comprises positioning the at least one auditory relay unit at a first end of the individual's body, and wherein the step of positioning the one or more vibrational units comprises positioning the one or more vibrational units at a second end of the individual's body, the first end of the individual's body being disposed generally opposite to the second end of the individual's body.

* * * * *